(12) United States Patent
Kumagai et al.

(10) Patent No.: US 11,357,398 B2
(45) Date of Patent: Jun. 14, 2022

(54) IMAGE PROCESSING DEVICE AND NON-TRANSITORY COMPUTER-READABLE RECORDING MEDIUM

(71) Applicant: NIDEK CO., LTD., Gamagori (JP)

(72) Inventors: Yoshiki Kumagai, Gamagori (JP); Tomohiro Miyagi, Gamagori (JP); Sohei Miyazaki, Gamagori (JP); Ryosuke Shiba, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 302 days.

(21) Appl. No.: 16/482,443

(22) PCT Filed: Jan. 30, 2018

(86) PCT No.: PCT/JP2018/002922
§ 371 (c)(1),
(2) Date: Jul. 31, 2019

(87) PCT Pub. No.: WO2018/143180
PCT Pub. Date: Aug. 9, 2018

(65) Prior Publication Data
US 2020/0069175 A1    Mar. 5, 2020

(30) Foreign Application Priority Data

Jan. 31, 2017  (JP) .............................. JP2017-016355
Jan. 31, 2017  (JP) .............................. JP2017-016356

(51) Int. Cl.
*A61B 3/10*    (2006.01)
*A61B 3/00*    (2006.01)
(Continued)

(52) U.S. Cl.
CPC ............ *A61B 3/102* (2013.01); *A61B 3/0025* (2013.01); *A61B 3/12* (2013.01); *A61B 3/14* (2013.01); *G06T 2207/30041* (2013.01)

(58) Field of Classification Search
CPC ......... A61B 3/102; A61B 3/0025; A61B 3/12; A61B 3/14; A61B 3/0041; G06T 2207/30041; G06T 1/00; G06T 7/00
(Continued)

(56) References Cited

U.S. PATENT DOCUMENTS

| | | | |
|---|---|---|---|
| 5,987,345 | A | 11/1999 | Engelmann et al. |
| 2011/0141436 | A1 | 6/2011 | Ono |

(Continued)

FOREIGN PATENT DOCUMENTS

| | | |
|---|---|---|
| JP | H10-155746 A | 6/1998 |
| JP | 2003-303240 A | 10/2003 |

(Continued)

OTHER PUBLICATIONS

Communication dated Aug. 25, 2020, from the Japanese Patent Office in counterpart application No. 2017-016355.
(Continued)

*Primary Examiner* — Mohammed A Hasan
(74) *Attorney, Agent, or Firm* — Sughrue Mion, PLLC

(57) ABSTRACT

An image processing device processes an image of a subject eye. The image processing device includes an image acquisition unit that acquires an image of the subject eye, a diagnosis unit that obtains a diagnosis result of the subject eye based on the image acquired by the image acquisition unit, and a display control unit that changes a display mode of a display unit based on the diagnosis result.

36 Claims, 9 Drawing Sheets

(51) Int. Cl.
    *A61B 3/12*    (2006.01)
    *A61B 3/14*    (2006.01)
(58) Field of Classification Search
    USPC .......................................................... 351/206
    See application file for complete search history.

(56)          References Cited

U.S. PATENT DOCUMENTS

2014/0185009 A1*   7/2014  Imamura .............. A61B 3/1025
                                                      351/208
2015/0348287 A1*  12/2015  Yi ........................... G06F 17/13
                                                      382/131
2016/0335394 A1*  11/2016  Kawagishi ................ G06F 3/14

FOREIGN PATENT DOCUMENTS

JP        2011-125463 A      6/2011
JP        2014-128366 A      7/2014
JP        2014-155875 A      8/2014
JP        2015-104581 A      6/2015
JP        2015-216939 A     12/2015
JP        2016-214324 A     12/2016

OTHER PUBLICATIONS

Akiko Kano "Development of a Computerized Image Processing System for the Aid of Diagnosis of Breast Cancer" retrieved from https://www.jstage.jst.go.jp/article/mll/21/1/21_1_79/_pdf, vol. 21, No. 1, 2004, (10 pages total).
Toshiaki Nakagawa et al. "Current status and issues of computer-aided diagnosis on retinal fundus images" retrieved from (https://www.jstage.jst.go.jp/article/mii/25/4/25_4_70/_pdf), vol. 25, No. 4, 2008, (14 pages total).
Koichi Sano "Image processing technology in medicine—Image diagnosis device centering on MRI" retrieved from (http://www.jstage.jst.go.jp/article/sicel1962/28/7/28_7_579/_pdf), vol 28, No. 7, 1989.
Rüdiger Bock et al. "Glaucoma risk index: Automated glaucoma detection from color fundus images" Medical Image Analysis, retrieved from https://www.sciencedirect.com/science/article/abs/pii/S1361841509001509 ), vol. 14, 2010, (pp. 471-481).
International Search Report (PCT/ISA/210) dated Apr. 10, 2018 issued by the International Searching Authority in International Application No. PCT/JP2018/002922.
Written Opinion (PCT/ISA/237) dated Apr. 10, 2018 issued by the International Searching Authority in International Application No. PCT/JP2018/002922.
Information Offer Form issued on Oct. 20, 2020 in the corresponding Japanese patent application No. 2017-016355.
Communication dated Aug. 4, 2020, from the Japanese Patent Office in counterpart application No. 2017-016356.

* cited by examiner

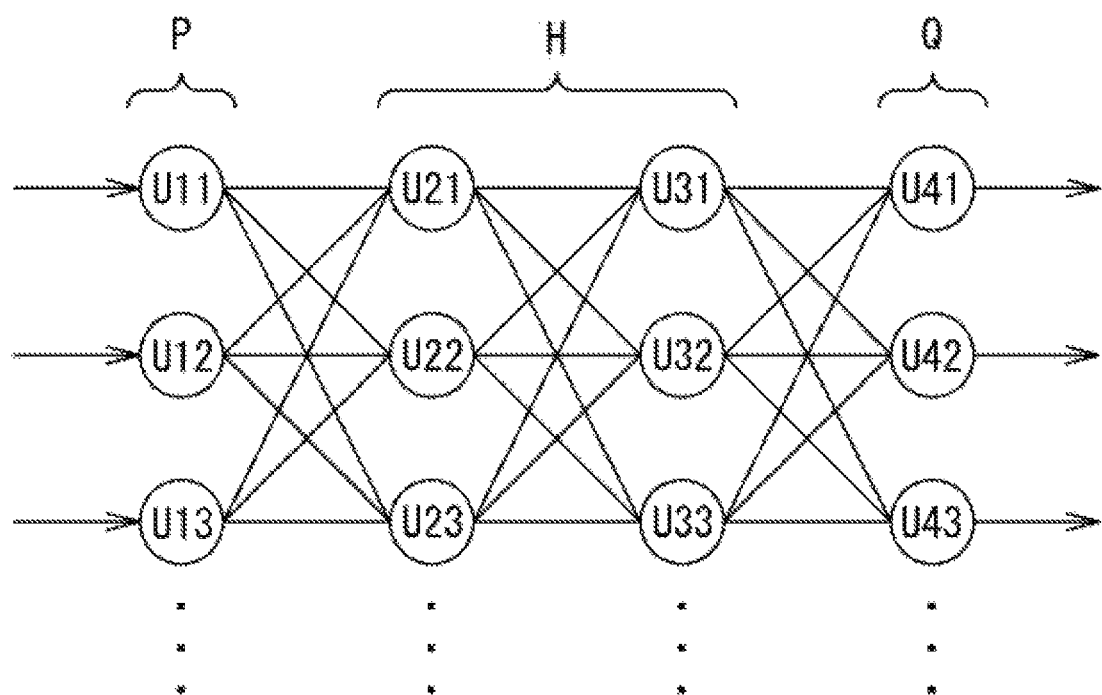

Fig. 4A
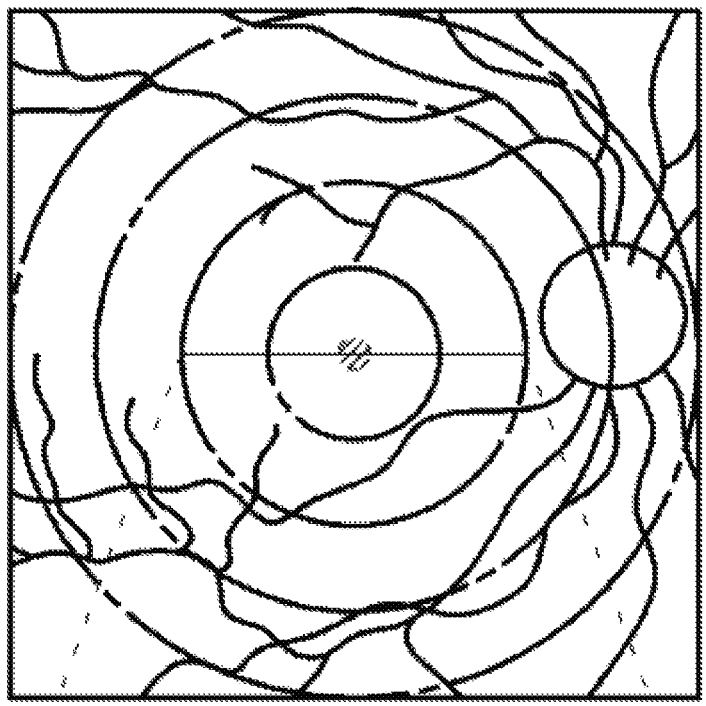
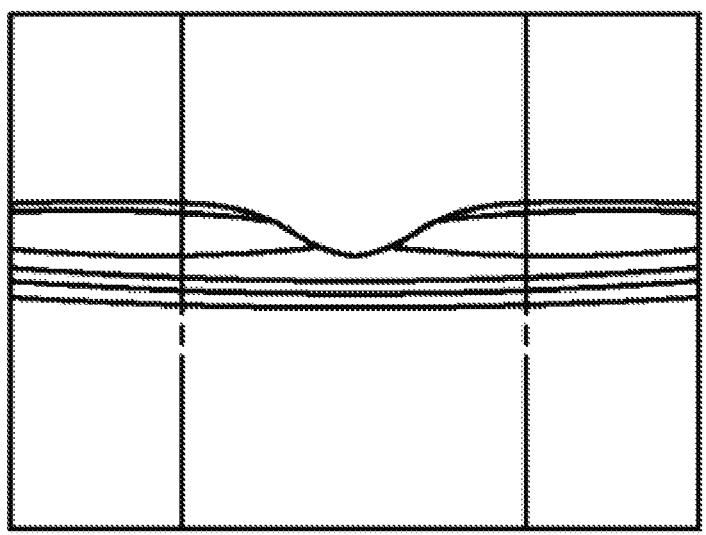

Fig. 4B
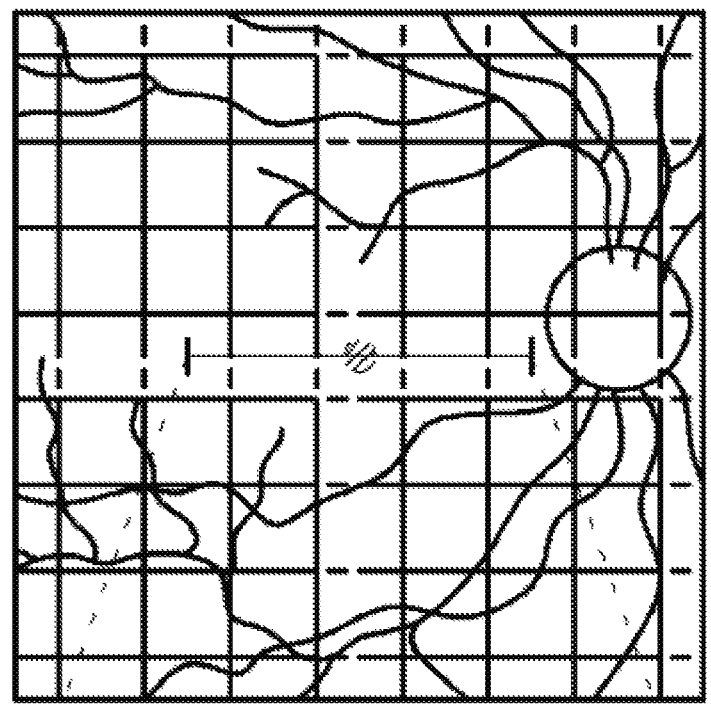
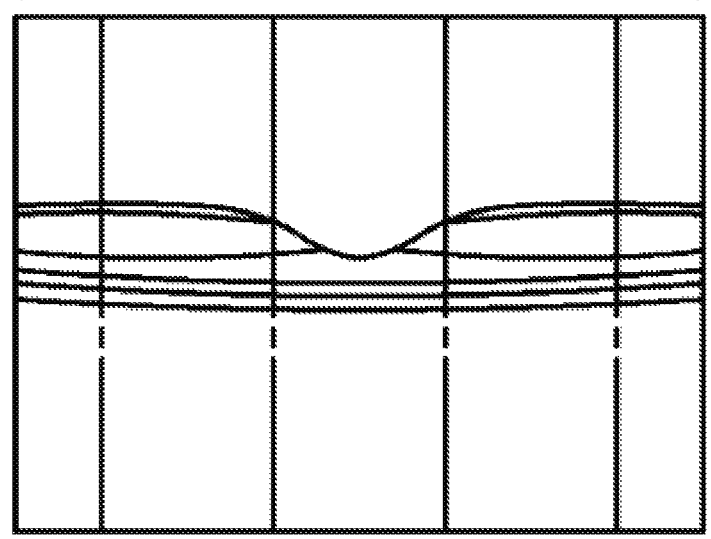

IMAGE PROCESSING DEVICE AND NON-TRANSITORY COMPUTER-READABLE RECORDING MEDIUM

TECHNICAL FIELD

The present disclosure relates to an image processing device for processing a captured image of a subject eye and a non-transitory computer-readable recording medium storing an image processing program.

BACKGROUND ART

In the related art, a diagnosis of a subject eye has been performed based on an image of the subject eye obtained by an ophthalmologic imaging device (for example, an optical coherence tomography, a fundus camera, or the like) and a result of analysis of the image.

CITATION LIST

Patent Literature

Patent Literature 1: JP-A-2015-104581

SUMMARY OF INVENTION

As a first problem, when diagnosing the subject eye, since the diagnosis is performed based on a display of a uniform result of analysis for every patient, the examiner has to see and compare all of the multiple results of analysis before finishing the diagnosis, and it becomes a burden.

As a second problem, when analyzing the image of the subject eye, since a shape of a retina significantly changes depending on the disease of the subject eye, in some cases, the image analysis cannot be performed.

The present disclosure has a technical subject to provide an image processing device and a non-transitory computer-readable recording medium storing an image processing program that solve at least one of the problems in the related art.

In order to solve the first problem, a first embodiment according to the present disclosure has following configurations.

(1) An image processing device, which processes an image of a subject eye, includes an image acquisition unit configured to acquire an image of the subject eye, a diagnosis unit configured to obtain a diagnosis result of the subject eye based on the image acquired by the image acquisition unit, and a display control unit configured to change a display mode of a display unit based on the diagnosis result.

(2) A non-transitory computer-readable recording medium stores an image processing program. The image processing program is executed in the image processing device which processes the image of the subject eye, which executed by a processor of the image processing device, the program causes the image processing device to perform an image acquisition step of acquiring an image of the subject eye, a diagnosis step of diagnosing the subject eye based on the image acquired in the image acquisition step, and a display control step of changing the display mode of a display unit based on a diagnosis result obtained in the diagnosis step.

In order to solve the second problem, a second embodiment according to the present disclosure has following configurations.

(3) An image processing device, which processes an image of a subject eye, includes an image acquisition unit configured to acquire an image of the subject eye, a diagnosis unit configured to obtain a diagnosis result of the subject eye, and an image processing unit configured to process the image with using a processing method according to the diagnosis result.

(4) An image processing device, which processes an image of a subject eye, includes an image acquisition unit configured to acquire an image of the subject eye, an image processing unit configured to specify an imaged part in the image and correct the image according to the specified imaged part, and a diagnosis unit configured to diagnose the subject eye based on the image corrected by the image processing unit.

(5) An image processing system includes an ophthalmologic imaging device that images a subject eye and an image processing device that processes an image of the subject eye. The system includes an image acquisition unit configured to acquire an image of the subject eye, a diagnosis unit configured to diagnose the subject eye based on the image acquired by the image acquisition unit, a selection unit configured to select a processing method for processing the image based on the diagnosis result obtained by the diagnosis unit, and an image processing unit configured to process the image with using the processing method selected by the selection unit.

(6) A non-transitory computer-readable recording medium stores an image processing program. The image processing program is executed in an image processing device which processes an image of a subject eye, when executed by a processor of the image processing device, the program causes the image processing device to execute an image acquisition step of acquiring an image of the subject eye, a diagnosis step of obtaining a diagnosis result of the subject eye, and an image processing step of processing the image using a processing method according to the diagnosis result.

BRIEF DESCRIPTION OF DRAWINGS

FIG. 3 is a diagram illustrating an example of a mathematical model.

FIG. 4A is a diagram illustrating a way how to divide an image.

FIG. 4B is a diagram illustrating a way how to divide an image.

DESCRIPTION OF EMBODIMENTS

First Embodiment

Figure 1:
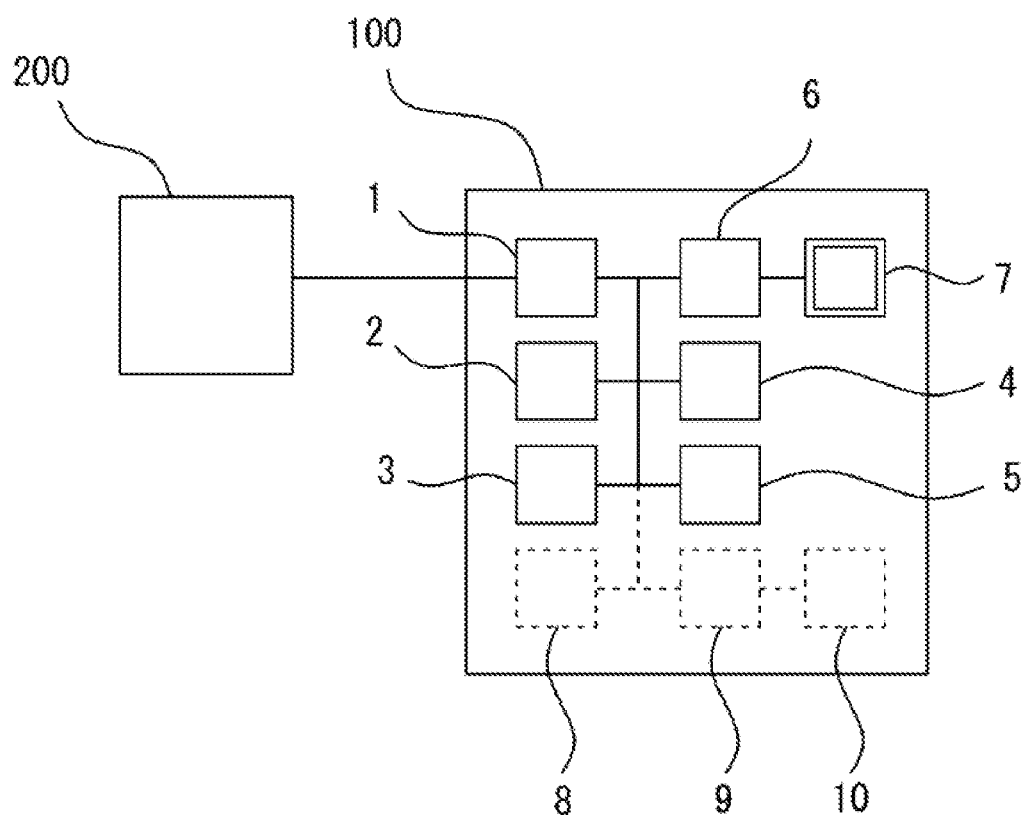
FIG. 1 is a schematic configuration diagram explaining a structure of an ophthalmologic imaging device according to a present embodiment.

Hereinafter, a first embodiment of an image processing device according to the present disclosure will be described.

The image processing device (for example, an image processing device 100) in the first embodiment acquires useful information for diagnosing a subject eye by processing the image of the subject eye. The image processing device includes, for example, an image acquisition unit (for example, an image acquisition unit 1), a diagnosis unit (for example, a diagnosis unit 2), an image processing unit (for example, an image processing unit 4), and the like.

For example, the image acquisition unit acquires an image of the subject eye. For example, the image acquisition unit is connected to the ophthalmologic imaging device or a storage unit through communication means such as wired (USB cable, LAN cable, IEEE 1394 cable, and the like) or wireless. A diagnosis unit (for example, a diagnosis processing unit) diagnoses, for example, the subject eye. The image processing unit processes the image using a processing method in accordance with the result of diagnosis. As described above, since the image processing method in accordance with the result of diagnosis performed by the diagnosis unit is used, the image processing device in the first embodiment can perform the image processing using a method suitable for each disease.

The image processing device may further include a selection unit (for example, a selection unit 3). The selection unit selects the processing method for processing the image based on, for example, the result of diagnosis obtained by the diagnosis unit. In this case, the image processing unit processes the image of the subject eye with using the processing method selected by the selection unit. As described above, since the processing method based on the result of diagnosis is selected by the selection unit, the image processing device can easily perform the suitable image processing.

The diagnosis unit performs the diagnoses of the subject eye based on, for example, the image acquired by the image acquisition unit. In this case, for example, the diagnosis unit may perform the diagnosis using a mathematical model trained by a machine learning algorithm. As the machine learning algorithms, for example, a neural network, a random forest, boosting, a support vector machine (SVM), and the like are generally known.

The neural network is a method of imitating the behavior of a neural network of a biological body. The neural network includes, for example, a feed forward (forward propagation) neural network, an RBF network (radial basis function), a spiking neural network, convolutional neural network, a recurrence type neural network (recurrent neural network, feedback neural network, or the like), a probability neural network (Boltzmann machine, Bayesian network, and the like).

The boosting is a method in which a strong classifier is generated by combining a plurality of weak classifier. The strong classifier is constructed by simply learning the weak classifiers sequentially.

The random forest is a method in which multiple decision trees are learned and generated based on randomly sampled training data. When the random forest is used, branches of a plurality of decision trees previously learned as classifiers are taken, and an average of the results of each decision tree (or the majority) is obtained.

The SVM is a method in which a two-class pattern identifier is constructed using linear input elements. In the SVM, for example, parameters of linear input elements are learned according to a criterion (hyperplane separation theorem) of finding a margin maximizing hyperplane at which the distance between each data point becomes maximum from the training data.

The mathematical model refers to a data structure for predicting the relationship between input data and output data. The mathematical model is constructed by the training using a training data set. The training data set is a set of training data for input and training data for output. The training data for input is sample data input to a mathematical model. For the example, for the training data for input, the image of the subject eye captured in the past is used. The training data for output is sample data of values to be predicted by the mathematical model. For example, for the training data for output, the result of diagnosis such as a disease name or a position of lesion is used. When a certain training data for input is input, the mathematical model is trained such that the corresponding training data for output is output. For example, training updates the correlation data (for example, weight) between each input and output.

For example, the diagnosis unit obtains the output of the result of diagnosis of the subject eye by inputting the image into the mathematical model. For example, from the mathematical model, the probability corresponding to each disease is output. The diagnosis unit can automatically perform the image diagnosis with using the trained mathematical model.

The image processing unit may specify an imaged part in the image and correct the image according to the identified imaged part. For example, the image processing unit specifies the imaged part in the image based on a feature point (for example, fovea, optic papilla, corneal apex, and the like) of a biological body (for example, an eye ball). For example, by detecting the fovea centralis from the image, the imaged part of the eyeball in the image is specified. Then, the image processing unit corrects the image according to the specified imaged part. For example, the image processing unit may perform the position correction of the image according to the imaged part, or may perform the distortion correction of the image.

The diagnosis unit may diagnose the subject eye based on the image corrected by the image processing unit. By using the corrected image for the automatic diagnosis, it is possible to prevent the deterioration of the diagnosis accuracy due to the influence of the position or distortion of the image.

The image processing unit may divide the image into equal to or more than two regions with respect to the feature points of a biological body. The image may be divided into a plurality of concentric regions or a lattice-shape region, using, for example, with the fovea centralis as a reference point. It is possible to perform the appropriate diagnosis for each region by dividing the image into a plurality of regions. For example, since the image processing algorithm specialized for each region can be used, it is possible to improve the diagnosis accuracy. In addition, it is easy to consider information on the diseases that are likely to occur in the specified region.

The diagnosis unit may use the image before being divided and the divided images for inputting to the mathematical model. By performing the image diagnosis based on the images before and after being divided, it is possible to improve the automatic diagnosis accuracy.

Various types of images may be used for the image diagnosis. For example, there are a tomographic image, a fundus image, a blood vessel image, an anterior ocular segment image, and the like, and thus, there are various imaged parts. These images are captured by various ophthalmologic imaging device such as an OCT apparatus, a fundus camera, an anterior ocular segment observation camera, a slit lamp, and a shine proof camera. As described above, when the images having different modalities are used for machine learning, the imaged part in the image may be specified, and then, the position alignment or the correction of the image may be performed.

The selection unit may select an image processing algorithm as the processing method. A plurality of image processing algorithms are prepared to perform the image processing. The selection unit selects at least one of the plurality of image processing algorithms for example. In addition, the selection unit may select the parameters of the image processing algorithm. The parameters are values used for image processing such as a weighting coefficient, an identifier, an energy (a weight of graph), or a threshold value.

The image processing device in the first embodiment may include an operation reception unit and a sequence creation unit (for example, a sequence creation unit 8). The operation reception unit receives an operation by a user (the examiner). The operation reception unit is a user interface such as a mouse or a touch panel. The sequence creation unit creates a sequence based on user's operation information received by the operation reception unit. The sequence is an order for the inspection or the analysis. For example, the user creates the sequence according to his/her preference and causes the image processing device to use the sequence. When creating the sequence, for example, the examiner sets an imaging method (number of scans, scanning position, scanning angle, and the like), a detection method, a determination method, an analysis method, a display method, and the like.

The image processing device in the first embodiment may include an evaluation unit (for example, an evaluation unit 9). The evaluation unit evaluates the sequence created by the sequence creation unit. For example, the evaluation unit evaluates the sequence using the inspection time and inspection accuracy. Of course, an evaluation value set by the user may be assigned to the sequence. In addition, the sequence creation unit may create an efficient sequence such that the evaluation value becomes high.

The image processing device in the first embodiment may include a sharing unit (for example, a sharing unit 10). The sharing unit transmits or receives the sequence to, for example, a shared server connected to the network. In this way, the user can share the sequence with other users. In addition, the sharing unit may share the evaluation value of the sequence together with the sequence. In this way, the user can perform the inspection efficiently by selecting a sequence having the high evaluation value and causing the image processing device to execute the sequence.

The selection unit may select a detection target for the image. For example, a region selected in a certain image may be automatically selected from other images. In this way, it is possible to save an effort to select a specified part in each image such as a case when the specified part of the image is wanted to be displayed in an enlarged view, or the like.

The image processing unit may change a style of the image acquired by the image acquisition unit. The image processing unit may convert the style of the image to a style having another modality, for example. For example, the image processing unit may convert the fundus image captured by the OCT apparatus into a fundus image captured by the fundus camera. In addition, the image processing unit may convert the style of the image captured by a device made by a certain manufacturer into a style of a device made by another manufacturer. For example, the image processing unit can improve the diagnosis accuracy by unifying the style of the image used for the image diagnosis.

The mathematical model may be configured to include a mathematical model that performs the classification of the diseases in a rough basis and a mathematical model that performs a detailed classification. For example, in the mathematical model that performs the classification of the diseases in a rough basis, a rough result of diagnosis may be used, such as a diagnosis whether the disease is a macular disease or other diseases when the image of the entire fundus is input. In the mathematical model that performs the detailed diagnosis, the divided images or the rough result of diagnosis may be used as the training data for input, and the detailed results of diagnosis such as disease name, the position of lesion, and the pathological condition may be used as the training data for output.

The image processing device may configure the image processing system together with the ophthalmologic device that images the subject eye. In addition, for example, a processor of the image processing device may execute an image processing program. For example, the image processing program includes an image acquisition step, a diagnosis step, and an image processing step. The image acquisition step is, for example, a step of acquiring the image of the subject eye. The diagnosis step is, for example, a step of obtaining the result of diagnosis of the subject eye. The image processing step is, for example, a step of processing the image using a processing method according to the result of diagnosis. The image processing program may be stored in a storage unit or the like of the image processing device, or may be stored in an external storage medium.

Second Embodiment

Hereinafter, a second embodiment of the image processing device according to the present disclosure will be described. An image processing device (for example, an image processing device 100) in the second embodiment acquires useful information used for the diagnosis of the subject eye by processing the image of the subject eye. The image processing device includes, for example, an image acquisition unit (for example, an image acquisition unit 1), a diagnosis unit (for example, a diagnosis unit 2), a display control unit (for example, a display control unit 6), and the like.

The image acquisition unit acquires an image of the subject eye. The image acquisition unit is connected to the imaging device or the storage unit by communication means such as wired or wireless communication. The diagnosis unit (a diagnosis processing unit) diagnoses the subject eye based on the image acquired by the image acquisition unit. The diagnosis unit may perform the diagnosis of the subject eye using a mathematical model trained by, for example, the machine learning algorithm.

The display control unit changes a display form (for example, a screen configuration) of a display unit based on the result of diagnosis obtained by the diagnosis unit. For example, the display control unit may change a display layout, and may change display items. The display layout and the display items according to the result of diagnosis may be set in advance, or may be set by the user.

For example, if the subject eye has a macular disease, the display control unit may display a retinal thickness map. In this way, the user can easily check the retinal abnormalities such as retinal thickness deviation. In addition, for example, if the subject eye has a glaucoma, the display control unit may display a comparison screen of the subject eye and the normal eye. In this way, the user can easily check the progression of the glaucoma condition. In addition, for example, if the subject eye has the glaucoma, the display control unit may display an image of an anterior chamber angle of the subject eye. In this way, the user can easily check whether the anterior chamber angle of the subject patient is narrow. In addition, if the subject eye has a diabetic retinopathy, the display control unit may display a blood vessel image (angiography) of the fundus. In this way, it is possible to easily check an abnormality in the blood vessel of the fundus due to the generation of a new blood vessel.

The display control unit may display the lesion part detected by the diagnosis unit from the image in the enlarged view. In this way, the user can recognize the existence of the lesion part and can check the details immediately.

The display control unit may display a probability map indicating the position and a probability of the disease, or a grade map indicating the position and a grade (progression degree of the disease. By checking these maps, the user can easily grasp the status of the subject eye.

The display control unit may display a treatment method according to the diagnosis result. For example, eye drops to be prescribed, a position of laser irradiation, or the like may be displayed. As result, the treatment plan of the subject eye can be performed smoothly. In addition, when displaying the result of analysis, the display control unit may display a point of the interpreting the image. For example, the display control unit can reduce the possibility of missing a disease by displaying the checking items in an order.

The image processing unit may perform the image processing for unifying the styles of the two image: one is the image for which the learning is already finished by the mathematical model and the other is the image of the subject eye. In this way, the diagnosis accuracy is improved using the machine learning.

The processor of the image processing device may execute an image processing program. The image processing program includes, for example, an image acquisition step, a diagnosis step, and a display control step. The image acquisition step is, for example, a step of acquiring the image of the subject eye. The diagnosis step is a step of diagnosing the subject eye based on the image acquired in the image acquisition step. The display control step is a step of changing the display mode of the display unit based on, for example, the diagnosis result obtained in the diagnosis steps.

Application Example

Hereinafter, an application example of the image processing device according to the present disclosure will be described based on FIG. 1. The image processing device 100 in the application example performs diagnosis of the subject eye by the image processing. The image processing device 100 may be, for example, a general personal computer. The image processing device 100 is, for example, a desktop PC, a laptop PC, or a tablet PC. Of course, the image processing device 100 may be a server or the like. In addition, the image processing device 100 may be a computer stored inside the ophthalmologic imaging device or the like.

The image processing device 100 includes, for example, the image acquisition unit 1, the diagnosis unit 2, the selection unit 3, the image processing unit 4, the storage unit 5, the display control unit 6, the display unit 7, and the like. The image acquisition unit 1 acquires various images relating to the subject eye. The image acquisition unit 1 is connected to the ophthalmologic imaging device via a wired or a wireless communication. The ophthalmologic imaging device is an apparatus for imaging the subject eye such as an optical coherence tomography (OCT) and a shine proof camera for imaging the tomographic images, a fundus camera and a scanning laser opthalmoscope (SLO) for imaging the fundus images, a corneal shape measuring apparatus for imaging the anterior ocular segment images, an ultrasonic diagnosis apparatus for imaging the ultrasound images, and the like. The ophthalmologic imaging device transmits the captured image of the subject eye to the image acquisition unit 1. The image acquisition unit 1 receives an image of the subject eye from each ophthalmologic imaging device and stores the image in the storage unit 5 or the like. The image acquisition unit 1 may acquire an image of the subject eye from an external storage device such as an HDD or a USB memory.

The diagnosis unit 2 diagnoses the subject eye based on the image acquired by, for example, the image acquisition unit 1. For example, the diagnosis unit 2 performs the image diagnosis with using the mathematical model trained by the machine learning algorithm. The machine learning algorithms are for example, the neural networks, the random forests, the boosting, the support vector machines (SVM), and the like. For example, the mathematical model is trained to output a probability of an appearance of symptoms in the subject eye due to various diseases by inputting the image of the subject eye. The diagnosis unit 2 obtains the output of the result of diagnosis by inputting the image of the subject eye to the mathematical model.

The selection unit 3 selects the processing method of the image based on the diagnosis result obtained by diagnosis unit 2. Here, the selection of the processing method includes a case of selecting a necessary image processing algorithm from a plurality of image processing algorithms and a case of selecting a parameter to be used for the image processing algorithm. The image processing algorithm may be an image processing algorithm constructed by the machine learning, or may be an artificially designed image processing algorithm.

The image processing unit 4 processes various images acquired by the image acquisition unit 1. The image processing unit 4 processes the image according to the processing method selected by the selection unit 3. For example, the image processing unit 4 performs various image processing such as image processing for segmentation of retinal layer, image processing for analyzing a retinal thickness, image processing for comparing the retinal thickness with that of the normal eye, image processing for detecting the blood vessel. The result of analysis acquired by image processing performed by the image processing unit 4 is sent to the display unit 7 or the storage unit 5 or the like.

The storage unit 5 stores various programs relating to the control of the image processing device 100, various image data, results of diagnosis, and the result of analysis. The display unit 7 displays the image acquired by the image acquisition unit 1, the diagnosis result, the analysis result, and the like. The display unit 7 may be a touch panel display. In this case, the display unit 7 is also used as an operation unit (an operation reception unit). The display control unit 6 controls the display on the display unit 7.

The image acquisition unit 1, the diagnosis unit 2, the selection unit 3, the image processing unit 4, the storage unit 5 and the display control unit 6 may be realized by various programs executed by the processors (for example, a CPU, or the like) of the computer used as the image processing device 100, or may be provided as independent control boards.

<Control Operation>

Figure 2:
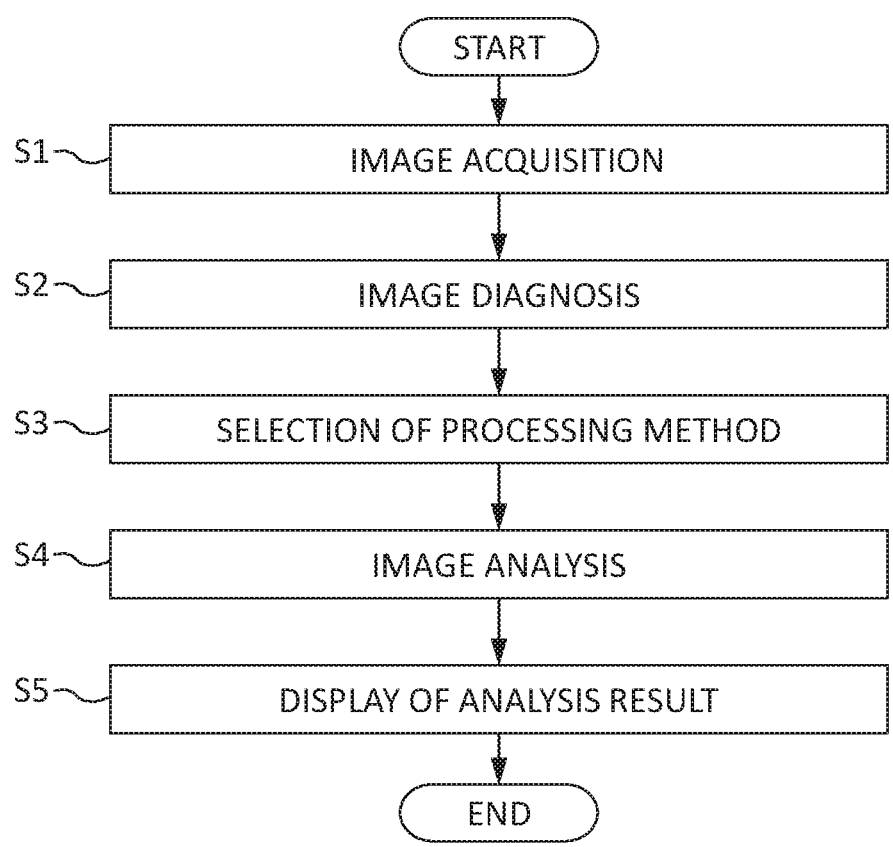
FIG. 2 is a diagram illustrating a flowchart of a control operation.

A control operation when the image processing device 100 in the present application example performs the image processing will be described based on FIG. 2. In the example described below, a case of using a tomographic image captured by the OCT apparatus 200 will be described. The OCT apparatus 200 is an apparatus for acquiring the tomographic image of the retina using, for example, interference between the returning light obtained by irradiating the fundus with the near-infrared measurement light and the reference light corresponding to the measurement light. Not limited to the tomographic images captured by the OCT apparatus 200, but other types of images may be used.

(Step S1: Image Acquisition)

First, the image acquisition unit 1 acquires an image of the subject eye to be used for the image diagnosis. A tomographic image of the subject eye is acquired from the storage unit 5 or the like of the OCT apparatus 200 connected by, for example, a USB cable or the like. Of course, the image data may be acquired using the USB memory or the like. The image acquisition unit 1 stores the acquired image in the storage unit 5 or the like.

(Step S2: Image Diagnosis)

Subsequently, the diagnosis unit 2 performs the diagnosis of the subject eye based on the acquired image. The diagnosis unit 2 performs the image diagnosis with using the mathematical model trained by, for example, the machine learning algorithm. As examples of the mathematical models used for the image processing, for example, a multi-layered neural networks and the like are known.

For example, the neural network is configured to include an input layer P for inputting the data, an output layer Q for generating the data to be predicted, and one or more hidden layers H between the input layer P and the output layer Q, and a plurality of nodes (also called as units) are arranged in each layer (see FIG. 3). Each node receives a plurality of inputs and calculates one output. For example, the data input to each node of each layer is output to each node of the adjacent layer. At this time, weights assigned to each path are different from each other. For example, the output value transmitted from one node to the next node is boosted or attenuated by the weight assigned to each path. When the weighted data is input to a node is output to each node of the next layer after a function such as an activation function is applied. This input and output is repeated between the adjacent layers, and predicted data is finally output from the output layer.

For example, if the nodes of the first layer are indicated as i=1, . . . , I, and the nodes of the second layer are indicated as j=1, . . . J, as expressed in equation (1) below, the total inputs uj received by the nodes in the second layer is a value obtained by adding all the values obtained by multiplying each input xi of the first layer by different weights wji, and then, adding a value bi called a bias to the result thereof.

$$u_j = \sum_{I=1}^{I} w_{ji} x_i + b_i \quad (1)$$

In addition, as expressed in equation below, the output zi of the node of the second layer is the output of the function f such as the activation function for the total input ui. Examples of the activation functions include functions such as a logistic jigmoid function, a hyperbolic tangent function, a normalized linear function, and a max out function.

$$z_i = f(u_j) \quad (2)$$

With the mathematical model in the neural network described above, the training is performed using a training data set, and thus, it is possible to perform the predictions about the new data. The training data set is a set of training data for input and the training data for output, and when the training data for input is input to the input layer, the weight and the bias of each node of each layer are adjusted such that a value close to the training data for output is output from the output layer. Since a plurality of training data sets are prepared, by the weight and bias being repeatedly adjusted, the general purpose weight and bias for various data can be obtained, it is possible to output the predicted values even for unknown data. The training of the mathematical model is continued until the error between the output against the input of the training data for input and the corresponding training data for output falls within an acceptable range. A back propagation (error back propagation method) or the like is used for the adjustment of the weight.

For example, when determining the presence or absence of a disease from the image of the subject eye, the training is performed using a plurality of training data sets configured from one set of a plurality of images of the subject eye and the results of diagnosis of the subject eye, or the like. In this case, a plurality of nodes corresponding to each pixel are provided in the input layer, and the pixel values are input respectively. A plurality of nodes corresponding to each disease are provided in the output layer, and each node outputs the probability corresponding to each disease. The diagnosis result to be used for training data for output may include the state of the disease, the position of the disease, and the like. Accordingly, the state of the disease or the position may be output to the mathematical model with respect to the input of the image.

The diagnosis unit 2 reads the image of the subject eye acquired by the image acquisition unit 1 from the storage unit 5 and inputs the image to each node of the input layer. The diagnosis unit 2 acquires the probability of each disease calculated according to the rule of the mathematical model from the output layer. The diagnosis unit 2 stores the output result of diagnosis in the storage unit 5.

As described above, when using a neural network, a convolutional neural network (CNN), which is a type of multi-layered neural network, may be used. The CNN is a mathematical model that includes the convolution processing and pooling processing, and is often used particularly in the field of image processing, and is often used particularly in the field of image processing. For details, refer to JP-A-10-21406 or JP-A-2015-032308.

The image diagnosis may be an automatic diagnosis based on the machine learning, or may be a diagnosis performed by the user checking the image of the subject eye with the display unit 7. In this case, for example, the user inputs the diagnosis result to the image processing device 100 through the operation unit such as the touch panel. When performing the automatic diagnosis using the machine learning, questionnaire information of the patient or imaging information (for example, setting of the OCT scanning, or the like) may be used. Of course, information of a plurality of modalities other than the OCT may be used.

(Step S3: Selection of Processing Method)

When the result of diagnosis performed by the diagnosis unit 2 is obtained, the selection unit 3 selects the processing method of the image according to the diagnosis result. That is, the processing method of the image is switched by the selection of the selection unit 3 switches. For example, the selection unit 3 selects at least one method from a plurality of image processing methods stored in the storage unit 5. For example, a plurality of image processing algorithms designed according to disease of the subject eye, state of the disease, position, or the like are stored in the storage unit 5, and each state of the disease is associated with the corresponding image processing algorithm. Thus, the selection unit 3 selects an image processing algorithm corresponding to the result of diagnosis of the subject eye.

When selecting the image processing method, the selection unit 3 may select an image processing algorithm with different parameters depending on the disease, or may change the image processing algorithm itself. In the former case, for example, the selection unit 3 selects the mathematical model (for example, the segmentation algorithm or the like) in which the parameters learned from the diabetic patient data are used if the diagnosis result is diabetes, and selects the mathematical model in which the parameters learned from AMD patient data are used if the diagnosis result is AMD (Age-related Macular Degeneration). The parameters are, for example, a graph weight, a threshold value used for the processing, or the like. In the latter case, for example, the selection unit 3 selects the image processing algorithm learned from the patient data if the disease is diabetes in which the structure of the retina is largely disintegrated, and selects an image processing algorithm such as a shortest path search or a graph search such as a graph cut, an active contour model such as a level set or a snake, or an edge detection such as Canny method if the eye is a normal eye or the disease is glaucoma in which the structure of the retina is almost unchanged.

(Step S4: Image Analysis)

When the method of processing the image is selected by selection unit 3, the image processing unit 4 performs the image processing with using the selected processing method. For example, the image processing unit 4 reads out the image processing algorithm selected by selection unit 3 from storage unit 5 and analyzes the image of the subject eye.

(Step S5: Display of Analysis Result)

When the image processing is performed by the image processing unit 4, the display control unit 6 causes the display unit 7 to display the result. For example, the examiner performs a diagnosis of the subject eye based on the result of analysis of the image displayed on the display unit 7.

As described above, the image processing device 100 in the present application example can perform image analysis using a method of analysis suitable for the case by performing the automatic diagnosis using the diagnosis unit 2 prior to the detailed image analysis. Therefore, the image processing device 100 can improve the success rate of the image analysis and provide the examiner with more appropriate diagnosis information.

In the related art, an examiner performed the diagnosis based on an image captured by the OCT apparatus 200 or the like and a quantitative value (such as a retinal thickness or a papillary C/D ratio) obtained by analyzing the image. However, since the form of the retina significantly changes depending on the disease, it is difficult to deal with all the diseases with using the specific image processing algorithm. When the algorithm is based on knowledge of a normal eye, for example, the analysis will fail if the retinal structure is broken due to the disease. In addition, depending on the type of image and imaging conditions, if the image processing is performed on all possible disease candidates that may appear in the image, and if the image diagnosis is performed based on these results, it takes much time to analyze. In addition, even with the same disease, since the degree of progression and symptoms differs depending on the patient, there is a possibility that the image processing may fail. Therefore, by switching the image processing algorithm based on the automatic diagnosis using the machine learning as in this application example, it is possible to perform the image processing efficiently.

The diagnosis unit 2 may perform automatic diagnosis again based on the detailed result of analysis obtained by the image processing unit 4. That is, a provisional diagnosis may firstly be performed by the diagnosis unit 2, and then, the diagnosis unit 2 may perform the final diagnosis again based on the result of analysis obtained by the method of analysis according to the diagnosis result. In this sway, the image processing device 100 can perform the automatic diagnosis more accurately.

In the automatic diagnosis using the machine learning, the position information on the fundus may be used. In this case, it is preferable to unify the coordinate system regarding the image used for the machine learning and the image of the subject eye. In particular, when using the images having different modalities, it is effective to unify the coordinate system of each image. For example, the coordinate systems may be unified with respect to the feature points of a biological body such as fovea centralis, or optic papilla. For example, the image processing unit 4 detects the fovea centralis in the acquired tomographic image. The fovea centralis has a smaller recessed shape than the optic papilla. Therefore, the image processing unit 4 detects a small depression shape from the tomographic image and assumes that as the fovea centralis. If the fovea centralis cannot be determined due to a disease or the like, the position of the fovea centralis may be estimated by estimating the shape of the eyeball from the peripheral region of the fundus or the kerato value or the like. If it is not possible to detect the fovea centralis automatically, it can be manually designated. When the position of the fovea centralis is specified, the processing unit 4 matches the position of each image with the respect to the position as a reference. In addition, the distortion correction of the image may be performed according to the imaged part. As described above, the position information of the image can be used by unifying the coordinate system of the image, and thus, it is possible to improve the accuracy of the disease classification or the automatic diagnosis.

The image processing unit 4 may divide the image based on the reference point. For example, the image processing unit 4 may divide the image into a plurality of concentric regions (FIG. 4A) or lattice shaped regions (FIG. 4B). In addition, the concentric regions may be further divided into radial shape. When dividing the image, the diagnosis unit 2 may use the divided images as the input data for the automatic diagnosis by the machine learning. In this way, it is possible to easily realize the automatic diagnosis in consideration of the position information of the image (imaged part). The diagnosis unit 2 may use an image before being divided for the automatic diagnosis as the input data together with the divided images.

The image processing device 100 may be able to set a sequence (flow of operation by the device) arbitrarily. For example, the image processing device 100 may include a sequence creation unit 8 (refer to FIG. 1) for creating the sequence. The sequence creation unit 8 may automatically create a sequence using the machine learning, or may create a sequence based on the examiner's operation. For example, the sequence creation unit 8 may create a sequence that can perform regular inspections with a small number of operations based on the examiner's operation history. The sequence creation unit 8 may create a sequence relating to the diagnosis or the analysis to be performed by the image processing device 100, or may create a sequence relating to the imaging to be performed by the ophthalmologic imaging device. That is, the sequence created by the sequence creation unit 8 can be applied to an ophthalmologic imaging system including the ophthalmologic imaging device and the image processing device 100 and the like. The sequence is determined by a combination of, for example, the imaging method (for example, scanning angle or the number of images, or the like), the detection (for example, the detection target, the detection method, the parameters of image processing algorithm, or the like), the determination method, display contents, or the like.

The diagnosis unit 2 or the image processing unit 4 performs the diagnosis and the analysis in accordance with the sequence set arbitrarily. The image processing device 100 may include an evaluation unit 9 that evaluates the sequence. The evaluation unit 9 evaluates the sequence created by the sequence creation unit 8. The evaluation unit 9 evaluates the sequence based on the processing time, the burden on the patient (the time required for imaging, or the like), the accuracy (evaluated by the doctor at the time of diagnosis), and the like, and stores the sequence in the storage unit 5 or the like. In addition, the image processing device 100 may include a sharing unit 10 that shares a sequence. For example, the sequence created by the sequence creation unit 8 may be released to other users via a network. At this time, an evaluation value assigned to the evaluation unit 9 may be released together with the sequence. The sharing unit 10 may obtain a sequence released by other users. In addition, for example, the sequence creation unit 8 may create a sequence that performs another inspection in addition to the usual inspection based on other examiner's operation history.

The selection unit 3 may select a detection target in the image based on the result of diagnosis performed by the diagnosis unit 2. For example, if the diagnosis result is glaucoma, because the anterior chamber angle may be narrow, the selection unit 3 selects the anterior chamber angle as a detection target when an anterior ocular segment tomographic image is input to present to the examiner. As described above, the selection unit 3 can perform the diagnosis and the analysis efficiently by selecting a part that is important for the diagnosis of each disease as the detection target.

Figure 5A:
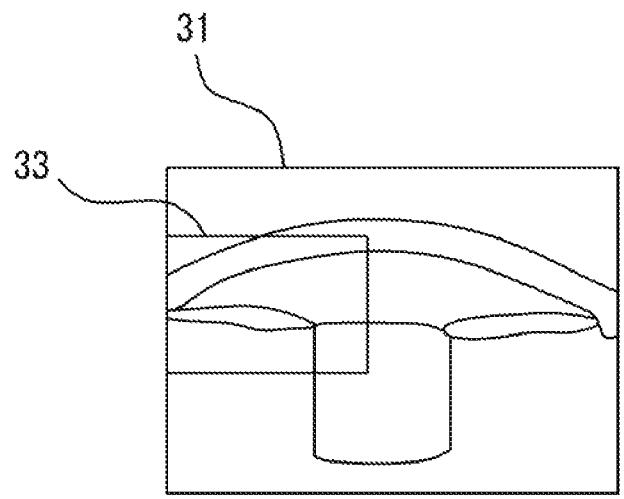
FIG. 5A is a diagram illustrating an example of an analysis screen displayed on a display unit.
Figure 5B:
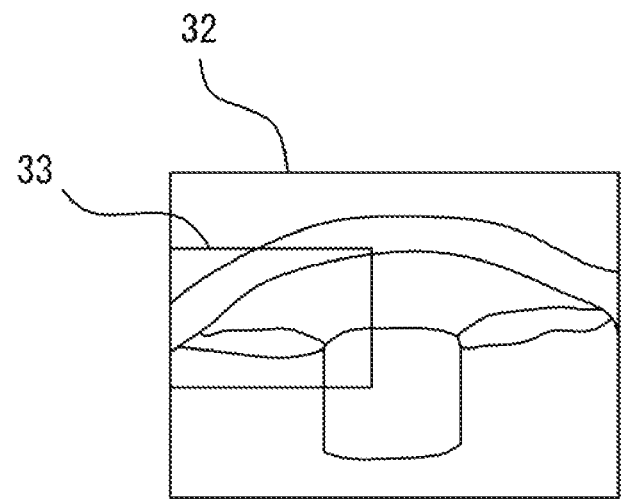
FIG. 5B is a diagram illustrating an example of an analysis screen displayed on a display unit.

The detection target in the image may be set by the user. For example, by selecting a region in one or more images, the user can detect a corresponding region in another image. For example, as illustrated in FIG. 5A, in a certain anterior ocular segment tomographic image 31, the user operates the operation unit such as a touch panel to place a cursor 33 for selecting the detection target on the region of the anterior chamber angle part, and sets the detection target. In this case, even in another anterior segment tomographic image 32, the image processing unit 4 detects the anterior chamber angle corresponding to the region designated in the anterior ocular segment image 31 as the detection target (refer to FIG. 5B). For example, the image processing unit 4 detects a portion in the anterior ocular segment tomographic image 32 that matches the feature of the image in the cursor 33 in the anterior ocular segment tomographic image 31. As described above, by causing the features selected for one image to be detected for other images, the examiner can save the effort for specifying the detection target for each image, and thus, it is possible to efficiently obtain the information important for the diagnosis.

In STEP S5, the display control unit 6 may change the display mode of the display unit 7 according to the diagnosis result of the subject eye. Since the checking position and the analysis content differ depending on the disease, the display control unit 6 displays the information required by the examiner in an easy-to-see mode. For example, the display control unit 6 performs segmentation processing according to each disease, analysis for the glaucoma, the blood vessel density analysis (for retinal vein occlusion and the like), display of the position of interest and the like in the enlarged view.

Figure 6A:
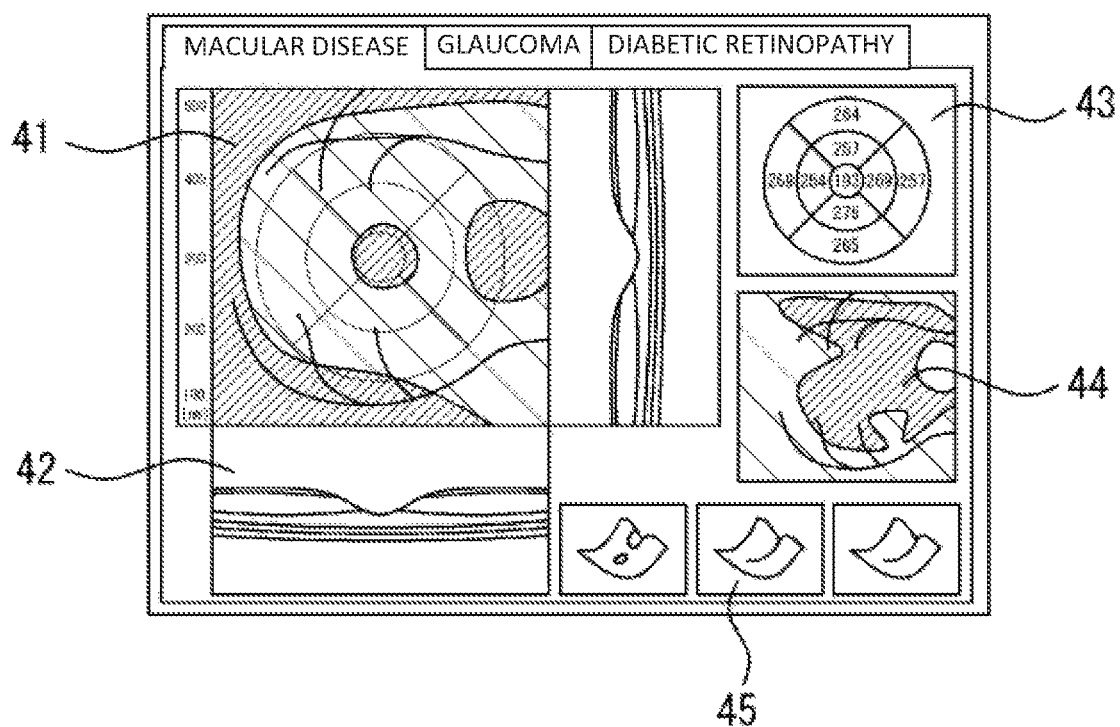
FIG. 6A is a diagram illustrating an example of a disease probability map.

For example, an example of changing the display layout will be described based on FIG. 6A and FIG. 6B. FIG. 6A is an example of a display layout displayed on the display unit 7 when the diagnosis result is the age-related macular degeneration. In a case of the macular diseases such as the age-related macular degeneration, the central serous chorioretinopathy, the retinal detachment, and the like, since there are abnormalities in the thickness of the retina, a thickness map 41 indicating the thickness of the retina is displayed on the display unit 7. In addition, a tomographic image 42, an analysis chart 43 of the retinal thickness, a comparison image 44 with the retinal thickness of a normal eye, a three-dimensional image of each retinal layer, and the like are displayed on the display unit 7. Even when the diagnosis result is the glaucoma, a comparison image 44 with the retinal thickness of the normal eye is displayed.

Figure 6B:
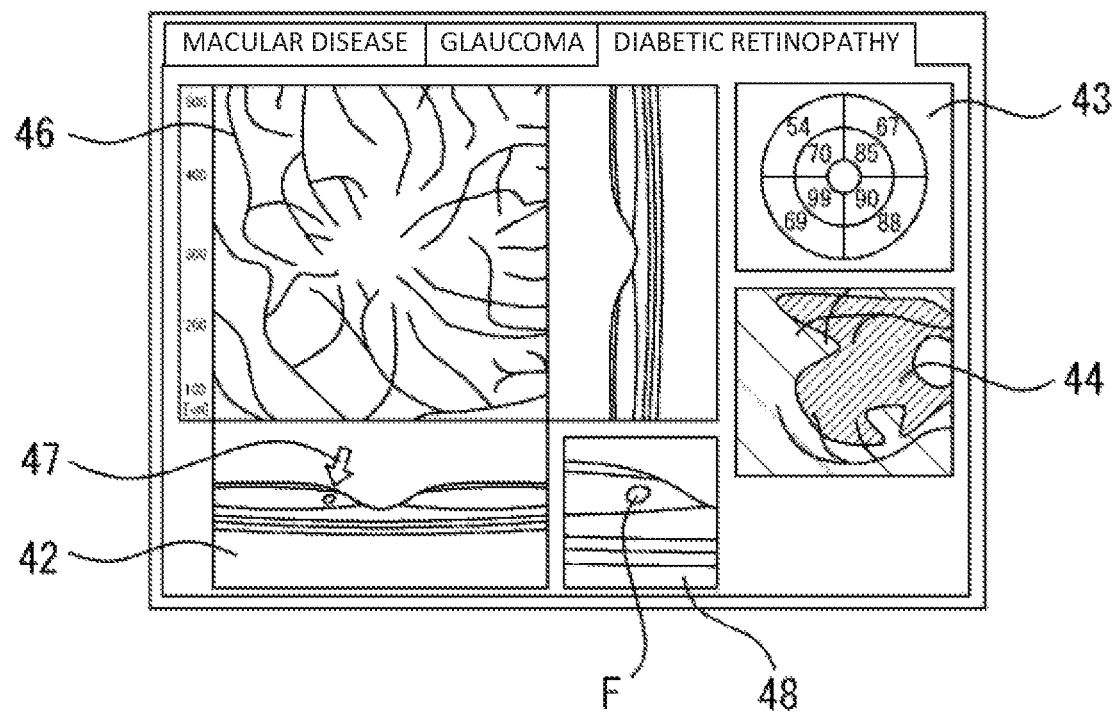
FIG. 6B is a diagram illustrating an example of a disease probability map.

FIG. 6B is a layout when the diagnosis result is the diabetic retinopathy. If the disease is suspected to be the diabetic retinopathy, since an abnormality in the blood vessel may be seen, thus, an OCT angiography 46 is displayed. This allows the examiner to check the abnormality in the blood vessel that is found in the diabetic retinopathy.

In addition, the display control unit 6 may display the position of the lesion part specified by the diagnosis and the analysis. For example, the display control unit 6 displays the position of the lesion part using a marker 47. In this way, it is possible to save the effort to operate the operation unit for the examiner to search for the lesion part. Furthermore, the display control unit 6 may display the lesion part in the enlarged view. For example, when a retinal edema F is present as illustrated in FIG. 6B, the display control unit 6 may display an enlarged image 48 of the part where the edema F is detected. In this manner, the region to be checked can be confirmed in detail by displaying the lesion part in the enlarged view.

As described above, by changing the display mode of the display unit 7 according to the diagnosis result, the operation for switching the display mode is reduced, and thus, it is possible to perform the efficient diagnosis, in addition, since the display control unit 6 causes the display unit 7 to mainly display the part where the disease is suspected, the examiner can perform the confirmation processing efficiently. In addition, even the less experienced users are less likely to miss the disease.

The display layout is not limited to those illustrated in FIG. 6A and FIG. 6B, and various display layouts can be considered. For example, the display layout according to the diagnosis result may be arbitrarily set by the examiner. In this case, the display control unit 6 reads out the display layout set in advance for each result of diagnosis and causes the display unit 7 to display the display layout. As illustrated in FIG. 6A and FIG. 6B, the display control unit 6 may arbitrarily switch the display layout set for each result of diagnosis by selecting the tabs or the like.

Figure 7:
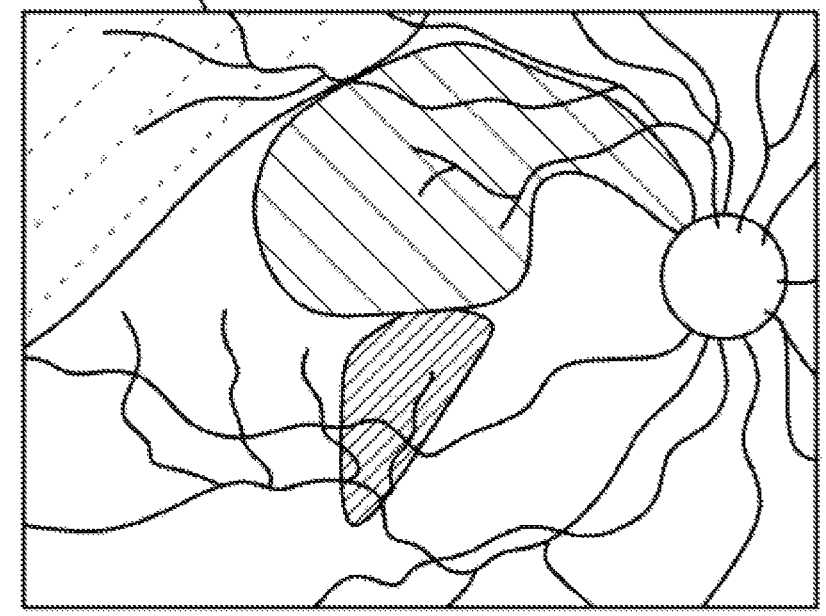
FIG. 7 is a diagram explaining a designation of a detection target.

The display control unit 6 may display a map indicating the grade or probability of the disease. For example, as illustrated in FIG. 7, it is acquired for the subject eye. For example, in the map 51, positions and probabilities of the appearance of symptoms are displayed in a color-coded view for each type of disease, and the color is darker as the probability increases. In this way, by displaying the map 51, the status of the subject eye can be easily checked.

The display layout is not limited to the example described above. For example, all the above-described images may be displayed on the screen, and the result of analysis relating to the diagnosed disease may be displayed in an enlarged or emphasized view. The display layout may be appropriately set by the user. The display layout set by the user may be released to other users via the network to be shared.

The display control unit 6 may cause the display unit 7 to display the diagnosis procedure. For example, with respect to the displayed image, the check items necessary for the diagnosis such as the color of the fundus and the retinal thickness may be displayed. In addition, when an operation indicating that the check is finished is performed, the following procedure may be displayed, and thus, it is possible to efficiently perform the diagnosis even in a case of inexperienced medical examination.

In addition, the display control unit 6 may cause the display unit 7 to display a proposal for the treatment according to the diagnosis result. For example, the display control unit 6 may cause the display unit 7 to display treatment methods and reference literatures according to the result of diagnosis performed by the diagnosis unit 2, or to display additional examination information necessary for increasing the accuracy of the disease name diagnosed by diagnosis unit 2. In addition, the display control unit 6 may cause the display unit 7 to display the position to be irradiated with the laser during the laser treatment.

In addition, the image processing unit 4 may analyze the same analysis in different ways, and may cause the result thereof to be stored or displayed. Generally, the time and the accuracy of analysis processing are in a trade-off relationship, and thus, in many cases, it takes a longer time for the high-accuracy analysis processing. Therefore, for certain analysis processing, the analysis may be performed with two algorithms such as the high-speed processing algorithm and the low-speed high-precision algorithm, and then, both results of analysis may be stored and switched to be appropriately displayed. For example, the high-speed analysis processing is performed by the image processing unit 4, and the result obtained by the high-speed algorithm is displayed on the checking screen after the imaging. In parallel, in the background, the low-speed high-accuracy analysis processing is performed by the image processing unit 4, and high-accuracy results are displayed during the medical examination. In this way, the highly accurate result of analysis that took the time can be provided, and it can felt that the waiting time is also reduced. The two results of analysis may be switched to be displayed or may be displayed simultaneously.

In addition, the image processing unit 4 may extract the feature amount from the blood vessel image acquired by the OCT apparatus 200, and may repeatedly perform the conversion of the blood vessel image such that the extracted feature amount approaches the feature amount of the fundus image captured by the fundus camera. In this way, the fundus blood vessel image acquired by the OCT apparatus 200 can be displayed as a fundus image captured by the fundus camera.

The image processing unit 4 may compose the blood vessel image and the color fundus image. In this case, the blood vessel image and the fundus image may be captured and the two images may be composed and displayed on the display unit 7.

The image processing unit 4 may convert the style of the image used for diagnosis. The image processing unit 4 changes the style of the image by adjusting, for example, the brightness, contrast or color of the image. In this way, even an image captured by a device different from the manufacturer can be used for the automatic diagnosis. For example, when using an image captured by a device of a certain manufacturer for learning a mathematical model, it may not be possible to determine the images captured by device of another manufacturer. However, by converting the image captured by the device of another manufacturer into the style of the image used for learning, the probability of obtaining an appropriate determination result is high. In other words, the images captured by other manufacturers can be used, and thus, the usable data can be greatly increased. In addition, the data can be linked between hospitals using the devices of different manufacturers.

In the application example described above, the tomographic image is used for the automatic diagnosis using the machine learning, however, it is not limited to thereto. For example, a fundus front image captured by the fundus camera, a scanning laser opthalmoscope or the like, or a blood vessel image (angiography) captured by an OCT apparatus may be used. In addition, a tomographic image captured by a Shine-proof camera, an anterior ocular segment image captured by an anterior ocular segment observation camera, a topographic image captured by a corneal shape measurement device, an fundus blood flow image obtained by a laser speckle imaging method (LSFG), or visual sensitivity information obtained by a microperimeter may be used for the machine learning.

The data used for the automatic diagnosis may be three-dimensional data as well as the two-dimensional data. For example, the machine learning based on the OCT map data (three-dimensional data) may be performed for the eyes of various disease and normal eyes, and the diagnosis may be performed based on any data regarding the subject eye. The deviation in each of the XYZ directions of each image used for input may be corrected by hardware (for example, tracking) or software.

In the application example described above, when performing the image diagnosis with using the machine learning algorithm, in addition to the image, feature parameters relating to the race, gender, age, genetic information, and the like may be input to the mathematical model.

In the application example described above, the image diagnosis was performed by a neural network, but not limited thereto. For example, other machine learning algorithms such as random forest, boosting may be used. For example, when the random forest is used, several decision trees determine the probability of disease respectively, and the final result of diagnosis is obtained by averaging the probability of diseases obtained from each decision tree. In addition, the disease of the subject eye may be classified with using the identifier obtained by boosting.

The image acquisition unit 1 may acquire the image from a server or the like. For example, a plurality of measurement results captured by multiple models may be stored in the server via the network, and the image acquisition unit 1 may be able to acquire the image data captured by another device from the server. For example, the image acquisition unit 1 may acquire the image from an electronic medical record system in which registration information and examination information and the like of patients are managed.

REFERENCE SIGNS LIST

100 image processing device
1 image acquisition unit 2 diagnosis unit
3 selection unit
4 image processing unit
5 storage unit
6 display control unit
7 display unit
200 OCT apparatus

The invention claimed is:

1. An image processing device that processes an image of a subject eye, comprising:
an image acquisition unit configured to acquire an image of the subject eye;
a diagnosis unit configured to obtain a diagnosis result of the subject eye based on the image acquired by the image acquisition unit; and
a display control unit configured to change a display mode of a display unit based on the diagnosis result,
wherein the display control unit causes the display unit to display a probability map indicating a position and a probability of a disease to be displayed, in which the position and the probability of the disease are displayed in a color-coded view for each disease, and the color is darker as the probability increases.

2. The image processing device according to claim 1, wherein the display control unit changes a display layout.

3. The image processing device according to claim 1, wherein the display control unit changes a display item.

4. The image processing device according to claim 1, wherein the display control unit causes a lesion part detected from the image to be displayed in an enlarged view.

5. The image processing device according to claim 1, wherein the display control unit causes a grade map indicating a position and a grade of a disease to be displayed.

6. The image processing device according to claim 1, wherein the display control unit causes a retinal thickness map to be displayed in a case where the diagnosis unit diagnoses that the subject eye has a macular disease.

7. The image processing device according to claim 1, wherein the display control unit causes a comparison screen of the subject eye and a normal eye to be displayed in a case where the diagnosis unit diagnoses that the subject eye has glaucoma.

8. The image processing device according to claim 1, wherein the display control unit causes an image of an anterior chamber angle of the subject eye to be displayed in a case where the diagnosis unit diagnoses that the subject eye has glaucoma.

9. The image processing device according to claim 1, wherein the display control unit causes a blood vessel image of a fundus to be displayed in a case where the diagnosis unit diagnoses that the subject eye has diabetic retinopathy.

10. The image processing device according to claim 1, wherein the display control unit causes a treatment method according to the diagnosis result to be displayed.

11. A non-transitory computer-readable recording medium storing an image processing program that is executed in an image processing device which processes an image of a subject eye, when executed by a processor of the image processing device, the program causing the image processing device to perform:
an image acquisition step of acquiring an image of the subject eye;
a diagnosis step of diagnosing the subject eye based on the image acquired in the image acquisition step; and
a display control step of changing a display mode of a display unit based on a diagnosis result obtained in the diagnosis step,
wherein the display control step causes the display unit to display a probability map indicating a position and a probability of a disease to be displayed, in which the position and the probability of the disease are displayed in a color-coded view for each disease, and the color is darker as the probability increases.

12. An image processing device that processes an image of a subject eye, comprising:
an image acquisition unit configured to acquire an image of the subject eye;
a diagnosis unit configured to obtain a diagnosis result of the subject eye;
an image processing unit configured to process the image using a processing method according to the diagnosis result; and
a display control unit configured to change a display unit to display a probability map indicating a position and a probability of a disease, in which the position and the probability of the disease are displayed in a color-coded view for each disease, and the color is darker as the probability increases.

13. The image processing device according to claim 12, further comprising:
a selection unit configured to select a processing method for processing the image based on the diagnosis result,
wherein the image processing unit processes the image with using the processing method selected by the selection unit.

14. The image processing device according to claim 13, wherein the selection unit selects at least one of a plurality of image processing algorithms prepared to process the image.

15. The image processing device according to claim 13, wherein the selection unit selects a parameter of an image processing algorithm for processing the image.

16. The image processing device according to claim 13, wherein the selection unit selects a detection target with respect to the image.

17. The image processing device according to claim 12, wherein the diagnosis unit obtains a diagnosis result of the subject eye based on the image of the subject eye acquired by the image acquisition unit.

18. The image processing device according to claim 12, wherein the diagnosis unit inputs the image into a mathematical model trained by a machine learning algorithm to obtain the diagnosis result of the subject eye output from the mathematical model.

19. The image processing device according to claim 12, wherein the image processing unit specifies an imaged part in the image and corrects the image of the subject eye according to the specified imaged part.

20. The image processing device according to claim 19, wherein the diagnosis unit diagnoses the subject eye based on the corrected image.

21. The image processing device according to claim 19, wherein the image processing unit divides the image in which the imaged part is specified into two or more regions with respect to a characteristic part of a biological body as a reference.

22. The image processing device according to claim 21, wherein the diagnosis unit diagnoses the subject eye based on the divided images.

23. The image processing device according to claim 21, wherein the diagnosis unit diagnoses the subject eye based on both the image before being divided and the divided images.

24. The image processing device according to claim 12, further comprising:
a sequence creation unit configured to create a sequence for operating the image processing device.

25. The image processing device according to claim 24, further comprising:
an operation reception unit configured to receive a user's operation,
wherein the sequence creation unit creates a sequence based on user's operation information received by the operation reception unit.

26. The image processing device according to claim 24, wherein the image processing unit performs processing based on the sequence.

27. The image processing device according to claim 24, comprising:
an evaluation unit configured to evaluate an efficiency of the sequence.

28. The image processing device according to claim 24, wherein the sequence creation unit creates the sequence based on an evaluation by the evaluation unit.

29. The image processing device according to claim 24, further comprising:
a sharing unit configured to transmit or receive the sequence to a shared server,
wherein the sequence is shared with another user.

30. The image processing device according to claim 12, wherein the image processing unit changes a style of the image acquired by the image acquisition unit.

31. An image processing device that processes an image of a subject eye, comprising:
an image acquisition unit configured to acquire an image of the subject eye;
an image processing unit configured to specify an imaged part in the image and correct the image according to the specified imaged part; and
a diagnosis unit configured to diagnose the subject eye based on the image corrected by the image processing unit.

32. The image processing device according to claim 31, wherein the image processing unit divides the image in which the imaged part is specified into two or more regions with respect to a characteristic part of a biological body as a reference.

33. The image processing device according to claim 32, wherein the diagnosis unit diagnoses the subject eye based on both the image before being divided and the divided images.

34. The image processing device according to claim 32, wherein the diagnosis unit diagnoses the subject eye based on the divided images.

35. An image processing system that includes an ophthalmologic imaging device that images a subject eye and an image processing device that processes an image of the subject eye, the system comprising:
an image acquisition unit configured to acquire an image of the subject eye;
a diagnosis unit configured to obtain a diagnosis result of the subject eye;
an image processing unit configured to process the image with using a processing method according to the diagnosis result; and
a display control unit configured to change a display unit to display a probability map indicating a position and a probability of a disease, in which the position and the probability of the disease are displayed in a color-coded view for each disease, and the color is darker as the probability increases.

36. A non-transitory computer-readable recording medium storing an image processing program that is executed in an image processing device which processes an image of a subject eye, when executed by a processor of the image processing device, the program causing the image processing device to execute:
an image acquisition step of acquiring an image of the subject eye;
a diagnosis step of obtaining a diagnosis result of the subject eye;
an image processing step of processing the image with using a processing method according to the diagnosis result; and
a display step that displays on a display unit a probability map indicating a position and a probability of a disease, in which the position and the probability of the disease are displayed in a color-coded view for each disease, and the color is darker as the probability increases.

* * * * *